(12) United States Patent
Zhang et al.

(10) Patent No.: US 12,085,100 B2
(45) Date of Patent: Sep. 10, 2024

(54) BOTTOM CYLINDER FOR HIGH-TEMPERATURE AND HIGH-PRESSURE ENVIRONMENT SIMULATOR

(71) Applicant: SICHUAN UNIVERSITY, Chengdu (CN)

(72) Inventors: Ru Zhang, Chengdu (CN); Zetian Zhang, Chengdu (CN); Zhilong Zhang, Chengdu (CN); Li Ren, Chengdu (CN); Chendi Lou, Chengdu (CN); Kun Xiao, Chengdu (CN); Anlin Zhang, Chengdu (CN); Qijun Hao, Chengdu (CN); Lanbin Zhang, Chengdu (CN)

(73) Assignee: SICHUAN UNIVERSITY, Chengdu (CN)

( * ) Notice: Subject to any disclaimer, the term of this patent is extended or adjusted under 35 U.S.C. 154(b) by 0 days.

(21) Appl. No.: 18/012,665

(22) PCT Filed: Aug. 22, 2022

(86) PCT No.: PCT/CN2022/113848
§ 371 (c)(1),
(2) Date: Dec. 23, 2022

(87) PCT Pub. No.: WO2023/051092
PCT Pub. Date: Apr. 6, 2023

(65) Prior Publication Data
US 2024/0102496 A1 Mar. 28, 2024

(30) Foreign Application Priority Data
Sep. 30, 2021 (CN) .......................... 202111161429.5

(51) Int. Cl.
*F15B 15/14* (2006.01)
*F15B 15/22* (2006.01)

(52) U.S. Cl.
CPC ...... *F15B 15/1428* (2013.01); *F15B 15/1447* (2013.01); *F15B 15/226* (2013.01); *F15B 15/1414* (2013.01); *F15B 15/1466* (2013.01)

(58) Field of Classification Search
CPC .............. F15B 15/1414; F15B 15/1419; F15B 15/1447; F15B 15/1466; F15B 15/226; F15B 15/261; F15B 2015/268
(Continued)

(56) References Cited

U.S. PATENT DOCUMENTS 2,891,513 A * 6/1959 Fagge .................... B23K 11/31
  92/84
3,033,171 A * 5/1962 Engelbrecht .......... F15B 15/261
  91/518
(Continued)

FOREIGN PATENT DOCUMENTS

CN 101415899 A 4/2009
CN 110762078 A 2/2020
(Continued)

*Primary Examiner* — Kenneth Bomberg
*Assistant Examiner* — Matthew Wiblin
(74) *Attorney, Agent, or Firm* — Bayramoglu Law Offices LLC

(57) ABSTRACT

A bottom cylinder for a high-temperature and high-pressure environment simulator of a high-fidelity corer is provided. The bottom cylinder includes a cylinder barrel. The bottom of the cylinder barrel is provided with a cylinder base. The piston is provided inside the cylinder barrel and divides an inner cavity of the cylinder barrel into a rodless cavity and a rod cavity. The piston is provided with a piston rod. The outer wall of the cylinder barrel is provided with an oil inlet hole communicated with the rodless cavity, an oil outlet hole communicated with the rod cavity, and a reserved hole. The lower end surface of the piston is provided with a first buffer ring, and the upper surface of the cylinder base is provided (Continued)

with a second buffer ring mated with the first buffer ring. The bottom cylinder is applied to the simulator for oil and gas resource exploitation.

8 Claims, 2 Drawing Sheets

(58) Field of Classification Search
USPC .................................................. 92/27, 85 R
See application file for complete search history.

(56) References Cited

U.S. PATENT DOCUMENTS

| | | | | |
|---|---|---|---|---|
| 3,231,255 | A * | 1/1966 | Olson | F16F 9/003 |
| | | | | 248/562 |
| 3,760,695 | A * | 9/1973 | Rothfuss | B25C 1/047 |
| | | | | 92/85 R |
| 3,969,989 | A * | 7/1976 | Maurer | B25C 1/04 |
| | | | | 92/85 R |
| 4,111,100 | A * | 9/1978 | Boyer | B29C 49/60 |
| | | | | 91/401 |
| 4,854,218 | A * | 8/1989 | Stoll | F15B 15/28 |
| | | | | 91/1 |
| 5,522,303 | A * | 6/1996 | Stoll | F15B 15/261 |
| | | | | 483/47 |
| 2002/0127532 | A1 * | 9/2002 | Eimori | G09B 5/04 |
| | | | | 434/350 |
| 2010/0162838 | A1 | 7/2010 | Hirai et al. | |

FOREIGN PATENT DOCUMENTS

| | | | |
|---|---|---|---|
| CN | 111425477 A | 7/2020 | |
| CN | 113883124 A | 1/2022 | |
| GB | 2274323 A * | 7/1994 | ........... F15B 15/063 |

* cited by examiner

BOTTOM CYLINDER FOR HIGH-TEMPERATURE AND HIGH-PRESSURE ENVIRONMENT SIMULATOR

CROSS REFERENCE TO THE RELATED APPLICATIONS

This application is the national phase entry of International Application No. PCT/CN2022/113848, filed on Aug. 22, 2022, which is based upon and claims priority to Chinese Patent Application No. 202111161429.5, filed on Sep. 30, 2021, the entire contents of which are incorporated herein by reference.

TECHNICAL FIELD

The present disclosure relates to the technical field of hydraulic cylinders, in particular, to a bottom cylinder for a high-temperature and high-pressure environment simulator.

BACKGROUND

In oil and gas resource exploitation and deep geological research, it is necessary to use a high-fidelity coring calibration platform to acquire deep in-situ high-fidelity rock cores to measure the physical and mechanical parameters of related rock formations. In the prior art, the high-fidelity coring calibration platform includes a simulator with a bottom cylinder to track and test basic physical and mechanical properties of rock samples to be drilled in the simulator at different temperatures and pressures of different depth.

However, in the prior art, most of the bottom cylinders are not provided with a buffer device. In actual oil and gas exploitation, due to the high-mass rock core, when the piston retracts to the cylinder bottom, it will cause a huge impact on the cylinder bottom, thus damaging the cylinder bottom and causing oil leakage. In the prior art, the cylinder is generally connected to the bottom of the simulator through a flange, which results in low assembly and disassembly efficiency and fails to meet the actual use requirement.

SUMMARY

In over to solve the above problems in the prior art, the present disclosure provides a bottom cylinder for a high-temperature and high-pressure environment simulator. The present disclosure solves the problems of most cylinders being directly applied to the high-temperature and high-pressure environment simulators in the prior art, such as oil leakage caused by damage to the cylinder bottom, low assembly and disassembly efficiency, and failure to meet the actual use requirement.

To achieve the above objective, the present disclosure adopts the following technical solution:

The bottom cylinder for a high-temperature and high-pressure environment simulator includes a cylinder barrel open at the top and the bottom, where the bottom of the cylinder barrel is provided with a cylinder base in a sealed manner. The piston is provided inside the cylinder barrel in a movable and sealed manner and divides an inner cavity of the cylinder barrel into a rodless cavity and a rod cavity.

The upper end surface of the piston is provided with a piston rod, and the piston rod has a top end passing through a top opening of the cylinder barrel and an outer wall connected to an inner wall of the cylinder barrel in a movable and sealed manner.

The outer wall of the cylinder barrel is provided with an oil inlet hole communicated with the rodless cavity, an oil outlet hole communicated with the rod cavity, and a reserved hole for a sensor wire in a simulator body to pass through.

The lower end surface of the piston projects downward to form a mounting post. The circumferential outer wall of the mounting post is provided with a first buffer ring, and the first buffer ring has an upper end surface connected to the lower end surface of the piston in a sealed and fixed manner and a lower end surface projecting from a lower end surface of the mounting post.

The upper surface of the cylinder base projects to form a second buffer ring positioned to mate with the first buffer ring, and the second buffer ring has a lower end surface connected to the upper surface of the cylinder base in a sealed and fixed manner and a circumferential sidewall connected to the inner wall of the cylinder barrel in a sealed and fixed manner.

Further, the upper end surface of the cylinder barrel is a stepped surface, and a clip mounting ring groove is provided on the circumferential outer wall at the top of the cylinder barrel.

Further, the clip mounting ring groove has an inclined sidewall at an angle of 2-5° with a horizontal plane.

Further, the inner cavity of the cylinder barrel has a cross-section in an inverted T shape. The piston is provided at the bottom of the inner cavity of the cylinder barrel, and the piston rod is provided at the top of the inner cavity of the cylinder barrel.

Further, a first sealing ring mounting groove is provided on the circumferential outer wall of the piston, and a sealing ring is provided in the first sealing ring mounting groove.

The circumferential inner wall at the top of the cylinder barrel is provided with multiple spaced-apart second sealing ring mounting grooves, each of which is provided therein with a sealing ring.

Further, the piston, the piston rod, and the mounting post are formed as a whole. The middle part of the lower end surface of the mounting post is provided with a first stop groove. The bottom of the first stop groove extends to the middle-upper part of the piston rod, and the length direction of the first stop groove is the same as the extension direction of the piston rod.

The upper end surface of the cylinder base is vertically provided with a stopper slidably connected to the first stop groove.

Further, the first stop groove has an isosceles-triangle or square cross-section and has a centerline coinciding with the centerline of the cylinder barrel. The stopper has a cross-section mated with the cross-section of the first stop groove.

Further, the lower end surface of the cylinder base is provided with multiple first countersunk threaded holes, and the outer edge of the upper surface of the cylinder base is provided with multiple second countersunk threaded holes.

Further, the top opening of the cylinder barrel is provided with a cylinder cover. The outer wall of the piston rod is connected to the cylinder barrel through the cylinder cover in a movable and sealed manner.

A locking ring groove is provided on the circumferential outer wall at the middle-lower part of the piston rod and has a right-triangle cross-section with a tipped bottom and a flat top.

A locking device is provided on the outer wall of the middle-lower part of the cylinder barrel. The locking device includes a push rod and a linear motor. A through hole for the push rod to pass through is provided on the outer wall of the cylinder barrel. The inner wall of the through hole is provided with a third sealing ring mounting groove, and a sealing ring is provided in the third sealing ring mounting groove.

The push rod has one end passing through the through hole and located inside the cylinder barrel, a circumferential outer wall connected to the through hole in a movable and sealed manner, and the other end fixedly connected to an output end of the linear motor. The linear motor is fixed to the outer wall of the cylinder barrel.

The locking element mated with the locking ring groove is provided on the end of the push rod inside the cylinder barrel and has a right-triangle cross-section.

The lower part of the locking ring groove is provided with a second stop groove, and the second stop groove has a rectangular cross-section and a width mated with the thickness of the locking element.

The length direction of the second stop groove is the same as the length direction of the piston rod, and the second stop groove has one end connected to the bottom of the locking ring groove and the other end extending to the bottom of the piston rod.

The present disclosure has the following benefits. 1. In this solution, the first buffer ring is provided at the bottom of the piston, and the second buffer ring is provided on the cylinder base. The cylinder is applied to the simulator for oil and gas resource exploitation, and the piston rod carries a large load due to the high-mass rock core in the simulator. When the piston retracts to the cylinder bottom, the first buffer ring contacts the second buffer ring to reduce the impact of the piston on the cylinder bottom to avoid damage to the cylinder bottom and oil leakage therefrom.

2. The upper end surface of the cylinder barrel is a stepped surface, which eases the sealed connection with the simulator. The clip mounting ring groove is provided on the circumferential outer wall at the top of the cylinder barrel. Grooved clips are clamped at the connection between the cylinder barrel and the simulator. Compared with the cylinder which is generally connected to the bottom of the simulator through a flange in the prior art, the bottom cylinder of the present disclosure has high assembly and disassembly efficiency and meets the actual use requirement.

3. The piston, the piston rod, and the mounting post are formed as a whole. The inner walls of the piston, the piston rod, and the mounting post are provided with the first stop groove. The first stop groove is mated with the stopper on the cylinder base to limit the rotational freedom of the piston rod. When the cylinder is in operation, the stopper cooperates with the first stop groove to guide the piston rod to move, thus effectively avoiding deflection of the extending piston rod.

4. In this solution, the outer wall of the cylinder barrel is provided with the locking device. Under the action of the linear motor, the top of the locking element contacts the bottom of the second stop groove to limit the rotation of the piston rod. When the piston rod extends to a certain position, the locking element is mated with the locking ring groove. When the rodless cavity leaks, the piston rod retracts under a load. However, the top of the locking element contacts the top of the locking ring groove to lock the piston rod and prevent the piston from continuing to retract and directly impact the cylinder base. When the piston rod needs to be fully retracted into the cylinder barrel, the linear motor is started to drive the locking element out of the locking ring groove to release the piston rod.

5. The cylinder barrel is provided with a reserved hole. An aviation plug is provided at a section of the reserved hole through a sealing ring mated with a tapered thread. The aviation plug isolates an interior of the reserved hole from a high-temperature and high-pressure environment at the upper part of the cylinder and also successfully transmits a sensor signal in the high-temperature and high-pressure environment from the upper part of the cylinder to an external normal-temperature and normal-pressure environment to meet some special requirements of the cylinder and the high-temperature and high-pressure simulator at the upper part.

Figure 1:
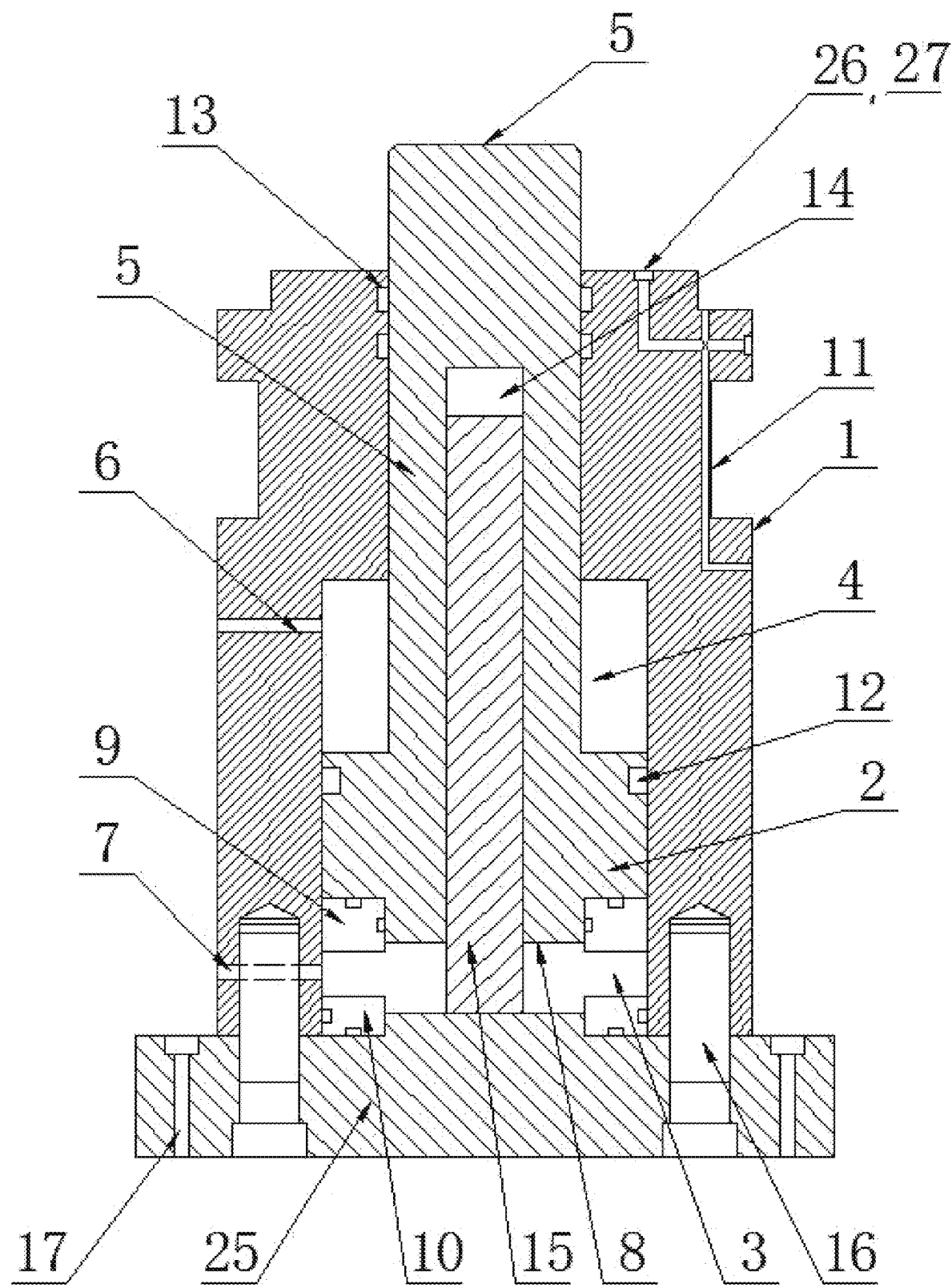
FIG. 1 is a section view of a bottom cylinder according to Embodiment 1 of the present disclosure.

Reference Numerals: 1. cylinder barrel; 2. piston; 3. rodless cavity; 4. rod cavity; 5. piston rod; 6. oil inlet hole; 7. oil outlet hole; 8. mounting post; 9. first buffer ring; 10. second buffer ring; 11. clip mounting ring groove; 12. first sealing ring mounting groove; 13. second sealing ring mounting groove; 14. first stop groove; 15. stopper; 16. first countersunk threaded hole; 17. second countersunk threaded hole; 18. cylinder cover; 19. locking ring groove; 20. push rod; 21. linear motor; 22. third sealing ring mounting groove; 23. locking element; 24. second stop groove; 25. cylinder base; and 26. reserved hole.

DETAILED DESCRIPTION OF THE EMBODIMENTS

The specific implementations of the present disclosure are described below to facilitate those skilled in the art to understand the present disclosure, but it should be clear that the present disclosure is not limited to the specific implementations. Various obvious changes made by those of ordinary skill in the art within the spirit and scope of the present disclosure defined by the appended claims should fall within the protection scope of the present disclosure.

Embodiment 1

Figure 2:
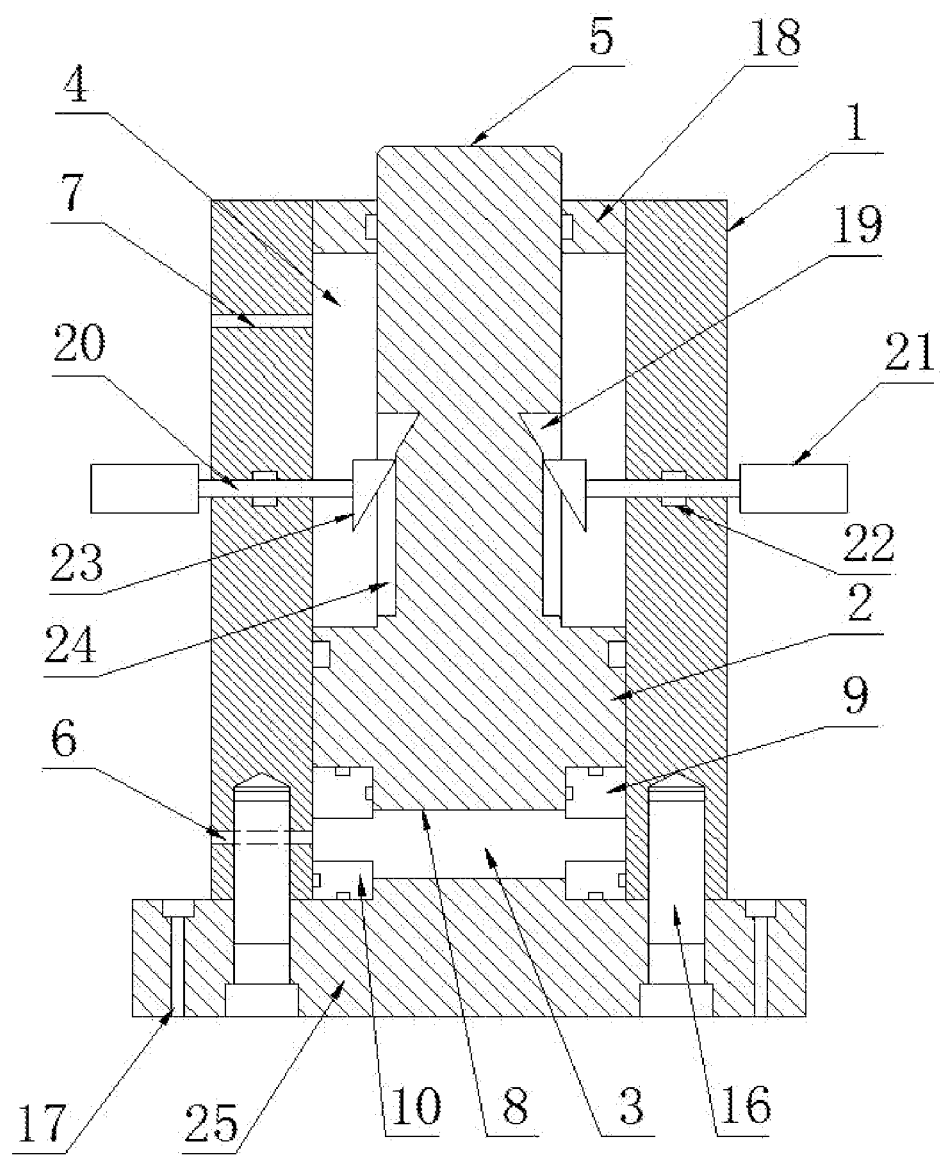
FIG. 2 is a section view of a bottom cylinder according to Embodiment 2 of the present disclosure.

As shown in FIGS. 1 to 2, this embodiment provides a bottom cylinder for a high-temperature and high-pressure environment simulator. The bottom cylinder includes cylinder barrel 1 open at the top and the bottom. The bottom of the cylinder barrel 1 is provided with cylinder base 25 in a sealed manner. Movable and sealed piston 2 is provided inside the cylinder barrel 1. The piston 2 divides an inner cavity of the cylinder barrel 1 into rodless cavity 3 and rod cavity 4.

The upper end surface of the piston 2 is provided with piston rod 5. The piston rod 5 has a top end passing through the top opening of the cylinder barrel 1 and an outer wall connected to the inner wall of the cylinder barrel 1 in a movable and sealed manner. The outer wall of the cylinder barrel 1 is provided with oil inlet hole 6 communicated with the rodless cavity 3 and oil outlet hole 7 communicated with the rod cavity 4.

The lower end surface of the piston 2 projects downward to form mounting post 8. A circumferential outer wall of the mounting post 8 is provided with first buffer ring 9. The first buffer ring 9 has an upper end surface connected to the lower end surface of the piston 2 in a sealed and fixed manner and a lower end surface projecting from a lower end surface of the mounting post 8.

The upper surface of the cylinder base 25 projects to form second buffer ring 10 positioned to mate with the first buffer ring 9. The second buffer ring 10 has a lower end surface connected to the upper surface of the cylinder base 25 in a sealed and fixed manner and a circumferential sidewall connected to the inner wall of the cylinder barrel 1 in a sealed and fixed manner.

In this solution, the first buffer ring 9 is provided at the bottom of the piston 2, and the second buffer ring 10 is provided on the cylinder base 25. The cylinder is applied to the simulator for oil and gas resource exploitation, and the piston rod 5 carries a large load due to the high-mass rock core in the simulator. When the piston 2 retracts to the cylinder bottom, the first buffer ring 9 contacts the second buffer ring 10 to reduce the impact of the piston 2 on the cylinder bottom to avoid damage to the cylinder bottom and oil leakage therefrom.

An upper end surface of cylinder barrel 1 is a stepped surface, which eases the sealed connection with the simulator. Clip mounting ring groove 11 is provided on a circumferential outer wall at a top of the cylinder barrel 1. Grooved clips are clamped at a connection between the cylinder barrel 1 and the simulator. Compared with the cylinder which is generally connected to the bottom of the simulator through a flange in the prior art, the bottom cylinder of the present disclosure has high assembly and disassembly efficiency and meets the actual use requirement.

The clip mounting ring groove 11 has an inclined sidewall at an angle of 2-5° with a horizontal plane. If the angle is too small, an upper end surface of the cylinder barrel 1 cannot be compressed with a flange of the simulator after the clips move close to each other, thus failing to achieve the sealing purpose. If the angle is too large, the sidewall of the clip mounting ring groove 11 will be excessively squeezed, causing deformation and damage.

The inner cavity of cylinder barrel 1 has a cross-section in an inverted T shape. The piston 2 is provided at the bottom of the inner cavity of the cylinder barrel 1, and the piston rod 5 is provided at the top of the inner cavity of the cylinder barrel 1. First sealing ring mounting groove 12 is provided on a circumferential outer wall of the piston 2, and a sealing ring is provided in the first sealing ring mounting groove 12. A circumferential inner wall at the top of the cylinder barrel 1 is provided with multiple spaced-apart second sealing ring mounting grooves 13, each of which is provided therein with a sealing ring.

The piston 2, the piston rod 5, and the mounting post 8 are formed as a whole. A middle part of the lower end surface of the mounting post 8 is provided with first stop groove 14. The bottom of the first stop groove 14 extends to the middle-upper part of the piston rod 5, and the length direction of the first stop groove 14 is the same as the extension direction of the piston rod 5. An upper end surface of the cylinder base 25 is vertically provided with stopper 15 slidably connected to the first stop groove 14. A cross-section of the first stop groove 14 is an isosceles triangle or a square, and the centerline of the first stop groove 14 coincides with the centerline of the cylinder barrel 1. A cross-section of the stopper 15 is mated with the cross-section of the first stop groove 14.

The piston 2, the piston rod 5, and the mounting post 8 are formed as a whole. The inner walls of the piston 2, the piston rod 5, and the mounting post 8 are provided with the first stop groove 14. The first stop groove 14 is mated with the stopper 15 on the cylinder base 25 to limit the rotational freedom of the piston rod 5. When the cylinder is working, the stopper 15 cooperates with the first stop groove 14 to guide the piston rod 5 to move, thus effectively avoiding deflection of the extending piston rod 5.

A lower end surface of the cylinder base 25 is provided with multiple first countersunk threaded holes 16. The multiple first countersunk threaded holes 16 are mated with countersunk bolts, such that the cylinder base 25 is threaded with the cylinder barrel 1, easing assembly and disassembly and improving work efficiency. An outer edge of the upper surface of the cylinder base 25 is provided with multiple second countersunk threaded holes 17. The cylinder base 25 is fixed on a mounting plane through the multiple second countersunk threaded holes 17.

The cylinder barrel 1 is provided with reserved hole 26. An aviation plug is provided at a section of the reserved hole 26 through a sealing ring mated with a tapered thread. The aviation plug isolates an interior of the reserved hole 26 from a high-temperature and high-pressure environment at an upper part of the cylinder and also successfully transmits a sensor signal in the high-temperature and high-pressure environment from the upper part of the cylinder to an external normal-temperature and normal-pressure environment to meet some special requirements of the cylinder and the high-temperature and high-pressure simulator at the upper part.

Embodiment 2

As shown in FIGS. 1 to 2, this embodiment provides a bottom cylinder for a high-temperature and high-pressure environment simulator. The bottom cylinder includes cylinder barrel 1 open at the top and the bottom. The bottom of the cylinder barrel 1 is provided with cylinder base 25 in a sealed manner. Movable and sealed piston 2 is provided inside the cylinder barrel 1. The piston 2 divides an inner cavity of the cylinder barrel 1 into rodless cavity 3 and rod cavity 4. An upper end surface of the piston 2 is provided with piston rod 5. The piston rod 5 has a top end passing through a top opening of the cylinder barrel 1 and an outer wall connected to the inner wall of the cylinder barrel 1 in a movable and sealed manner. An outer wall of the cylinder barrel 1 is provided with oil inlet hole 6 communicated with the rodless cavity 3 and oil outlet hole 7 communicated with the rod cavity 4. A lower end surface of the piston 2 projects downward to form mounting post 8. A circumferential outer wall of the mounting post 8 is provided with first buffer ring 9. The first buffer ring 9 has an upper end surface connected to the lower end surface of the piston 2 in a sealed and fixed manner and a lower end surface projecting from a lower end surface of the mounting post 8. An upper surface of the cylinder base 25 projects to form second buffer ring 10 positioned to mate with the first buffer ring 9. The second buffer ring 10 has a lower end surface connected to the upper surface of the cylinder base 25 in a sealed and fixed manner and a circumferential sidewall connected to the inner wall of the cylinder barrel 1 in a sealed and fixed manner.

When the piston 2 retracts to the cylinder bottom, the first buffer ring 9 contacts the second buffer ring 10 to reduce the impact of the piston 2 on the cylinder bottom to avoid damage to the cylinder bottom and oil leakage therefrom.

The top opening of the cylinder barrel 1 is provided with a cylinder cover 18. An outer wall of the piston rod 5 is connected to the cylinder barrel 1 through the cylinder cover 18 in a movable and sealed manner. Locking ring groove 19 is provided on a circumferential outer wall at the middle-lower part of the piston rod 5. A cross-section of the locking ring groove 19 is a right triangle with a tipped bottom and a flat top. A locking device is provided on an outer wall of the middle-lower part of the cylinder barrel 1. The locking device includes push rod 20 and linear motor 21. A through hole for the push rod 20 to pass through is provided on the outer wall of the cylinder barrel 1. An inner wall of the through hole is provided with third sealing ring mounting groove 22. A sealing ring is provided in the third sealing ring mounting groove.

One end of the push rod 20 passes through the through hole and is located inside the cylinder barrel 1. A circumferential outer wall of the push rod 20 is connected to the through hole in a movable and sealed manner. The other end of the push rod 20 is fixedly connected to an output end of the linear motor 21. The linear motor 21 is fixed to the outer wall of the cylinder barrel 1. Locking element 23 mated with the locking ring groove 19 is provided on the end of the push rod 20 inside the cylinder barrel 1. A cross-section of the locking element 23 is a right triangle. A lower part of the locking ring groove 19 is provided with a second stop groove 24. A cross-section of the second stop groove 24 is rectangular. The width of the second stop groove 24 is mated with the thickness of the locking element 23. The length direction of the second stop groove 24 is the same as the length direction of the piston rod 5. The second stop groove 24 has one end connected to a bottom of the locking ring groove 19 and the other end extending to a bottom of the piston rod 5.

In this solution, the outer wall of cylinder barrel 1 is provided with the locking device. Under the action of the linear motor 21, the top of the locking element 23 contacts the bottom of the second stop groove 24 to limit the rotation of the piston rod 5. When the piston rod 5 extends to a certain position, the locking element 23 is mated with locking ring groove 19. When the rodless cavity 3 leaks, the piston rod 5 retracts under a load. However, the top of the locking element 23 contacts the top of the locking ring groove 19 to lock the piston rod 5 and prevent the piston 2 from continuing to retract and directly impact the cylinder base 25. When the piston rod 5 needs to be fully retracted into the cylinder barrel 1, the linear motor 21 is started to drive the locking element 23 out of the locking ring groove 19 to release the piston rod 5.

What is claimed is:

1. A bottom cylinder for a high-temperature and high-pressure environment simulator, comprising a cylinder barrel, open at a top and a bottom, wherein the bottom of the cylinder barrel is provided with a cylinder base in a sealed manner; and a piston is provided inside the cylinder barrel in a movable and sealed manner, and the piston divides an inner cavity of the cylinder barrel into a rodless cavity and a rod cavity;
   an upper end surface of the piston is provided with a piston rod; and the piston rod has a top end and an outer wall, wherein the top end passes through a top opening of the cylinder barrel, and the outer wall is connected to an inner wall of the cylinder barrel in the movable and sealed manner;
   an outer wall of the cylinder barrel is provided with an oil inlet hole and an oil outlet hole, wherein the oil inlet hole is communicated with the rodless cavity, and the oil outlet hole is communicated with the rod cavity, and the outer wall of the cylinder barrel is provided with a reserved hole;
   a lower end surface of the piston projects downward to form a mounting post; a circumferential outer wall of the mounting post is provided with a first buffer ring; and the first buffer ring has an upper end surface and a lower end surface, wherein the upper end surface of the first buffer ring is connected to the lower end surface of the piston in a sealed and fixed manner, and the lower end surface of the first buffer ring projects from a lower end surface of the mounting post; and
   an upper surface of the cylinder base interfaces with a second buffer ring positioned to mate with the first buffer ring; and the second buffer ring has a lower end surface and a circumferential sidewall wherein, the lower end surface of the second buffer ring is connected to the upper surface of the cylinder base in a sealed and fixed manner, and the circumferential sidewall is connected to the inner wall of the cylinder barrel in the sealed and fixed manner.

2. The bottom cylinder according to claim 1, wherein an upper end surface of the cylinder barrel is a stepped surface, and a clip mounting ring groove is provided on the outer wall at the top of the cylinder barrel.

3. The bottom cylinder according to claim 2, wherein the clip mounting ring groove has an inclined sidewall at an angle of 2-5° with a horizontal plane.

4. The bottom cylinder according to claim 2, wherein the inner cavity of the cylinder barrel has a cross-section in an inverted T shape; the piston is provided at a bottom of the inner cavity of the cylinder barrel; and the piston rod is provided at a top of the inner cavity of the cylinder barrel;
   a first sealing ring mounting groove is provided on the outer wall of the piston, and a first sealing ring is provided in the first sealing ring mounting groove; and
   the inner wall at the top of the cylinder barrel is provided with a plurality of spaced-apart second sealing ring mounting grooves, each of the plurality of spaced-apart second sealing ring mounting grooves is provided therein with a second sealing ring.

5. The bottom cylinder according to claim 1, wherein the piston, the piston rod, and the mounting post are formed as a whole; a middle part of the lower end surface of the mounting post is provided with a first stop groove; a bottom of the first stop groove extends to a middle-upper part of the piston rod; and a length direction of the first stop groove is the same as an extension direction of the piston rod; and
   the upper surface of the cylinder base is vertically provided with a stopper slidably connected to the first stop groove.

6. The bottom cylinder according to claim 5, wherein the first stop groove has an isosceles-triangle or square cross-section, and the first stop groove has a centerline coinciding with a centerline of the cylinder barrel; and the stopper has a cross-section mated with the cross-section of the first stop groove.

7. The bottom cylinder according to claim 1, wherein a lower end surface of the cylinder base is provided with a plurality of first countersunk threaded holes; and an outer edge of the upper surface of the cylinder base is provided with a plurality of second countersunk threaded holes.

8. The bottom cylinder according to claim 1, wherein the top opening of the cylinder barrel is provided with a cylinder cover; and the outer wall of the piston rod is connected to the cylinder barrel through the cylinder cover in the movable and sealed manner;

a locking ring groove is provided on the outer wall at a middle-lower part of the piston rod and has a right-triangle cross-section with a tipped bottom and a flat top;

a locking device is provided on the outer wall of a middle-lower part of the cylinder barrel;

the locking device comprises a push rod and a linear motor; a through hole is provided on the outer wall of the cylinder barrel, wherein the through hole is for the push rod to pass through; an inner wall of the through hole is provided with a third sealing ring mounting groove; and a third sealing ring is provided in the third sealing ring mounting groove;

the push rod has a first end, a circumferential outer wall, and a second end, wherein the first end passes through the through hole and is located inside the cylinder barrel, the circumferential outer wall of the push rod is connected to the through hole in a movable and sealed manner, and the second end is fixedly connected to an output end of the linear motor; and the linear motor is fixed to the outer wall of the cylinder barrel;

a locking element is provided on the first end of the push rod inside the cylinder barrel, and has a right-triangle cross-section, wherein the locking element is mated with the locking ring groove;

a lower part of the locking ring groove is provided with a second stop groove; and the second stop groove has a rectangular cross-section, and has a width mated with a thickness of the locking element; and a length direction of the second stop groove is the same as a length direction of the piston rod; and the second stop groove has a first end-and a second end, wherein the first end is connected to a bottom of the locking ring groove, and the second end extends to a bottom of the piston rod.

* * * * *